United States Patent
Schaaf

(10) Patent No.: US 8,287,448 B2
(45) Date of Patent: Oct. 16, 2012

(54) ENDOSCOPE COMPRISING A FLEXIBLE PROBE

(75) Inventor: Hansgeorg Schaaf, Reichertshausen (DE)

(73) Assignee: Polydiagnost GmbH, Pfaffenhofen (DE)

( * ) Notice: Subject to any disclaimer, the term of this patent is extended or adjusted under 35 U.S.C. 154(b) by 1264 days.

(21) Appl. No.: 10/577,682

(22) PCT Filed: Nov. 18, 2003

(86) PCT No.: PCT/EP03/12897
§ 371 (c)(1),
(2), (4) Date: Sep. 5, 2008

(87) PCT Pub. No.: WO2005/051180
PCT Pub. Date: Jun. 9, 2005

(65) Prior Publication Data
US 2008/0312505 A1    Dec. 18, 2008

(30) Foreign Application Priority Data

Oct. 31, 2003 (DE) .................................. 103 51 013

(51) Int. Cl.
*A61B 1/00* (2006.01)
(52) U.S. Cl. ........ 600/146; 600/114; 600/139; 600/147; 600/148
(58) Field of Classification Search .......... 600/114–115, 600/146–148
See application file for complete search history.

(56) References Cited

U.S. PATENT DOCUMENTS

| | | | |
|---|---|---|---|
| 4,688,555 A * | 8/1987 | Wardle | 600/149 |
| 4,762,120 A | 8/1988 | Hussein | |
| 4,919,112 A | 4/1990 | Siegmund | |
| 4,941,455 A * | 7/1990 | Watanabe et al. | 600/146 |
| 4,984,563 A * | 1/1991 | Renaud | 600/108 |
| 5,156,590 A | 10/1992 | Vilmar | |
| 5,254,088 A * | 10/1993 | Lundquist et al. | 604/95.04 |
| 5,349,942 A | 9/1994 | Heimberger | |
| 5,441,483 A * | 8/1995 | Avitall | 604/95.05 |
| 5,549,542 A * | 8/1996 | Kovalcheck | 600/146 |
| 6,234,958 B1 * | 5/2001 | Snoke et al. | 600/114 |
| 6,319,195 B1 * | 11/2001 | Nakaichi et al. | 600/120 |
| 6,929,600 B2 * | 8/2005 | Hill | 600/120 |
| 6,979,290 B2 * | 12/2005 | Mourlas et al. | 600/115 |
| 7,591,813 B2 * | 9/2009 | Levine et al. | 604/528 |
| 2005/0272975 A1 * | 12/2005 | McWeeney et al. | 600/113 |

FOREIGN PATENT DOCUMENTS

| | | |
|---|---|---|
| DE | 32 16 178 A1 | 11/1983 |
| DE | 199 28 272 A1 | 1/2001 |
| DE | 199 56 516 A1 | 6/2001 |
| DE | 199 55 614 C1 | 7/2001 |
| DE | 201 18 886 U1 | 3/2002 |
| DE | 100 45 036 C1 | 7/2002 |
| DE | 102 41 946 A1 | 3/2003 |
| JP | 05-329216 | * 12/1993 |
| WO | WO 93/15648 A1 | 8/1993 |

* cited by examiner

OTHER PUBLICATIONS

International Search Report dated Jun. 21, 2004 (Four (4) pages).

*Primary Examiner* — Matthew J Kasztejna
(74) *Attorney, Agent, or Firm* — Crowell & Moring LLP

(57) ABSTRACT

An endoscope with a flexible, multilumen catheter probe, a grip provided at the proximal end of the probe, a control element attached to the distal end of the probe and movably guided in the axial direction on catheter probe, wherein the catheter probe is to be connected non-rotatily to the grip by means of a releasable lock, the distal end of the optical lumen has a transparent seal, and optical system is displacably disposed inside optic lumen and can be removed from optic lumen.

16 Claims, 5 Drawing Sheets

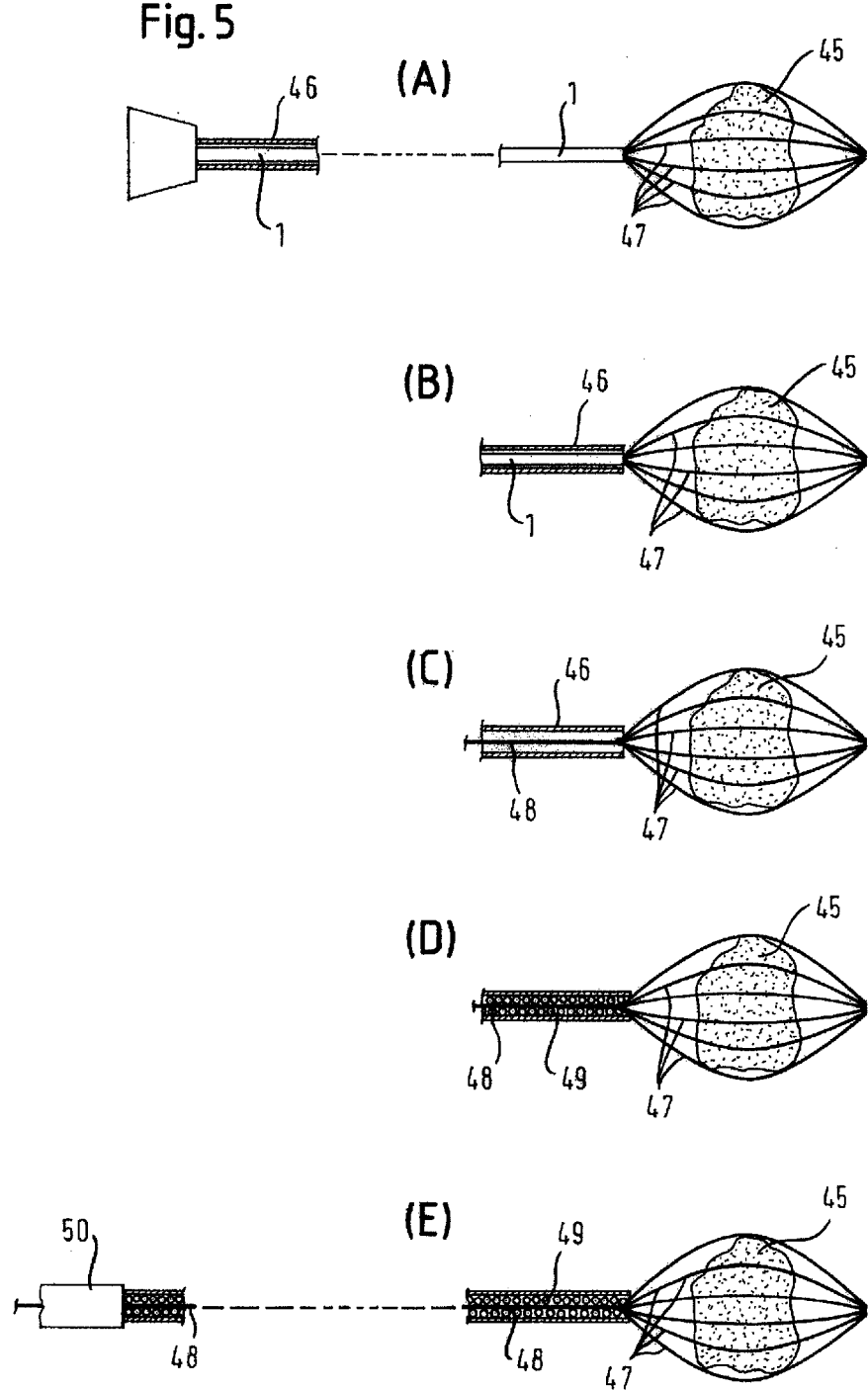

ENDOSCOPE COMPRISING A FLEXIBLE PROBE

BACKGROUND OF THE INVENTION

The invention relates to an endoscope comprising a flexible catheter probe with a plurality of lumens, in accordance with the generic part of claim 1.

Such an endoscope is known from DE 100 45 036 C1. This known endoscope has a multilumen probe and a grip provided at the proximal end of the probe. An optical system extends inside at least one of the probe lumens. A working lumen for a surgical instrument is also provided. A control element, for example in the form of a traction wire or a traction cable, is connected to the distal end of the probe and is movably guided on the probe in axial direction. In this way, a therapeutic endoscope is obtained that can be easily operated during a surgical operation.

An endoscope with a handle assembly and a catheter assembly is known from U.S. Pat. No. 4,762,120, in which the catheter assembly is rotatably and removably mounted the handle assembly. In the assembled state, the fiber optic provided in the catheter probe is aligned with the eyepiece optics provided in the handle assembly. This is achieved by removably connecting an optical outlet provided on the catheter assembly to the handle assembly. The catheter probe has a plurality of lumens whose outlets are located at the proximal end outside the handle assembly. A control element for guiding the probe to its destination is not provided in this endoscope.

Maintenance and especially decontamination of endoscopes with multilumen probes is very difficult. This results in high servicing costs, and ensuring decontamination causes long outage times between uses.

BRIEF SUMMARY OF THE INVENTION

The object of the invention is therefore to provide an endoscope with controllable and flexible multilumen probes that is easily maintained and with which difficulties with decontamination, in particular, are eliminated.

This object is achieved according to the invention by the characterizing features of claim 1.

Advantageous developments of the invention are defined in the subclaims.

In this invention, a rigid or torsion-resistant guide device for guiding the control element is non-rotatingly connected to the grip, in particular to the housing of the grip, at the proximal end of the probe by means of a releasable lock. The guide device preferably has a tubule shape, the control element being guided through the tubule cavity. The control element is also connected to a slider that is guided inside the grip, likewise releasably, by means of a releasable fixing means, for example a locking screw. At the distal end of the optical lumen in the probe, there is a light-transmitting seal or cover, for example in the form of a glass or plastic disk that is inserted into the lumen material to form a leakproof seal and hermetically seal the optical lumen at the distal end from the destination. The transparent cover can also have optical properties, in particular imaging properties, and be configured as a lens, for example. The transparent cover in the form of a disk or lens can be inserted into the distal opening of the optical lumen to form a hermetic seal by bonding or welding it into the probe material consisting of plastic, in particular, or by means of extrusion, injection molding or the like when forming the probe.

The optical system, in particular the illumination and observation optics, is displaceably and removably disposed inside the optical lumen. In order to move the optical system, a slider assembly such as the one known from DE 199 56 516 A1, for example, is provided at the proximal end of the probe, in particular at the optical outlet through which the waveguides/fiber optics are guided out of the optical lumen. To remove the optical system from the optical lumen, the slider assembly can be releasably attached to the optical outlet, for example by means of a bayonet lock or a Luer lock.

A different device may be used instead of a slider to compensate the length of the optical lumen when bending the distal end of the probe. This length compensation device acts on the waveguide/fiber optic bundle of the optical system, for example with a specific biasing force preferably exerted by a spring, and presses the waveguide/fiber optic bundle against the transparent cover at the distal end of the optical lumen.

When bending the distal end of the probe, the change in length is compensated by the biasing force of the spring, such that the optical system remains in position at the cover with a certain compressive force. When the distal end moves back into the starting position and alignment with the rest of the probe, the optical strand is returned to its starting position by moving against the biasing force of the spring.

In the invention, only the guide device for the control element is non-rotatingly connected to the grip or the grip housing. The proximal outputs for the other probe lumens are not joined to the grip. Said probe lumen outlets are independent of the grip and can be attached to associated terminal equipment externally from the grip. For example, the illumination optics fed through the optical outlet, which are also guided if necessary by the slider or length compensation device, are connected to an illumination system. The observation optics can be connected to an eyepiece that can preferably be attached to the grip. However, the observation optics can also be connected in known manner to a camera/monitor system, or to a suitable observation device.

In addition, a rinsing outlet can be connected at the proximal end of a rinsing lumen of the probe to a rinsing/evacuation system. A working lumen or a plurality of working lumens can also be connected to operating elements in order to receive a surgical instrument or several surgical instruments, and with which the respective surgical element is operated. For this purpose, the respective surgical element is removably guided inside the assigned working lumen.

The multilumen probe is preferably configured as a disposable part. The probe can be manufactured by injection-molding or extruder technology, or by any other suitable molding technology, and can be made of plastic. At the proximal end of the probe, an attachment member made of a non-elastic material, for example plastic, can also be provided on which the lumen outlets for the plurality of probe lumens and the guide outlet for the control element are provided. The lumen outlets and the guide outlet can preferably include connection elements for Luer locks, bayonet locks or the like. or be configured as coupling members of such locking connections, and likewise consist of the non-elastic material of the proximal attachment member. Preferably, the proximal attachment member can also be designed as an injection-molded or extruded part that forms a disposable part in combination with the flexible probe.

The surgical instrument which is removable from the working lumen can be easily decontaminated. The optical system removed from the optical lumen is not contaminated during the surgical operation, because the distal end of the optical lumen is protected by the transparent seal at the distal end opposite the destination, and the surrounding probe material protects the optical system in its longitudinal extension. Since the probe is preferably configured as a disposable part, a new, as yet unused probe is connected to the grip as described above when the endoscope is to be used once again.

The slider assembly, to which the control element in the grip is releasably connected, can preferably be moved by means of a crank assembly. The crank assembly can be operated on the outside of the grip with the help of an operating element provided on the grip, for example in the form of a pivotable lever or bar that is fixedly attached to the crank assembly. A locking device that is likewise operated on the outside of the grip can also be provided, with which the slider and in particular the crank assembly can be locked in desired and preferably continuously adjustable positions on the grip.

The operating elements for the slider and/or the crank assembly and the locking device are preferably configured symmetrically with respect to a center plane running through the grip. The grip housing is likewise symmetrical relative to said center plane. This ensures that the grip has the same shape and design for both left-handed persons and right-handed persons. A holder for an eyepiece connected to the observation optics can also be provided on the grip. This holder can be moved into different positions as desired by means of a pivot bearing, for example with a ball-and-socket joint.

BRIEF DESCRIPTION OF THE DRAWINGS

An embodiment of the invention shall now be explained in detail with reference to the Figures, which show:

FIG. 5 consecutive steps during mechanical lithotripsia with the aid of an embodiment of the invention.

DETAILED DESCRIPTION OF THE INVENTION

Figure 1:
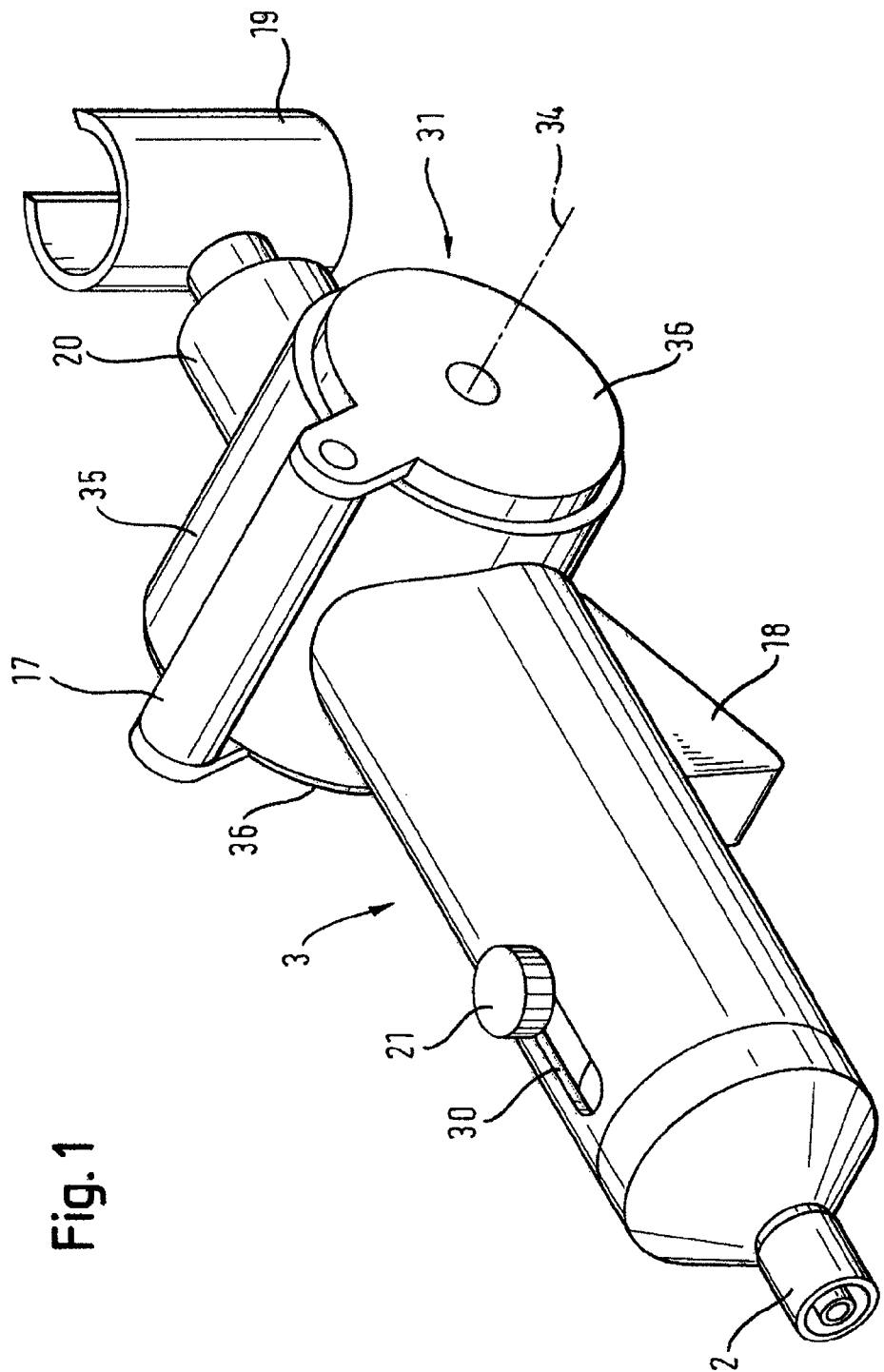
FIG. 1 an embodiment for a grip, seen at an angle from above in perspective view.

The embodiment of an endoscope shown in the Figures includes a grip 3 and a catheter probe 1 releasably attached to the grip. Probe 1 is configured as a multilumen probe and can comprise, for example, a working lumen or a plurality of working lumens 7 for surgical instruments, and at least one optical lumen 4 for an optical system 6. A rinsing lumen 27 for rinsing the destination and for extracting particles from the destination can also be provided inside the probe 1. Separate optical lumens can also be provided for the optical system 6 comprising illumination optics 22 and observation optics 23. Separate lumens for rinsing and extraction can likewise be provided in probe 1.

Catheter probe 1 also includes a control element 13, for example in the form of a traction cable or traction wire. As is known from DE 100 45 036 C1, for example, the elongated control element is fixedly attached to the distal end of the probe or to a point near the distal end, and extends in the axial direction along the probe and is movably guided on the probe. The distal end member of catheter probe 1 can be bent by means of said control element. The distal end of the probe, which can be bent by means of a control element, can also be configured in the manner known from DE 201 18 886 U or from DE 199 28 272 A1.

Catheter probe 1 consists of a pliable material, in particular of biocompatible plastic. It is preferably designed as a disposable part that is released from the grip and disposed of after a surgical operation. When a new surgical operation is to be carried out, a new catheter probe kept sterile in readiness as a disposable part is attached to grip 3.

At its proximal end, catheter probe 1 has a probe attachment member 8 made of a rigid, non-elastic material. This can likewise be a plastic material. Proximal lumen outlets 9, 10 and 11, as well as a tubule-shaped guide device 12 for control element 13 are disposed on the probe attachment member 8. Control element 13 is fed through the tubule cavity. Lumen outlet 9 is assigned, for example, to rinsing lumen 27, whereas lumen outlet 10 is assigned, for example, to working lumen 7, and lumen outlet 11 is assigned, for example, to optical lumen 4. The outlets are fitted in known manner with coupling elements, for example for a bayonet lock or Luer lock, or with similar coupling and connection pieces.

Catheter probe 1 is non-rotatingly connected to grip 3, in particular to the grip housing, via the rigid, tubule-shaped guide device 12 for control element 13. The grip has a lock member at its front end for this purpose, said lock member forming a releasable lock 2 when joined to a lock member provided on guide device 12. The releasable lock 2 can be a bayonet lock or a Luer lock. By means of releasable lock 2, a non-rotating connection is formed between grip 3 and catheter probe 1. In this way, rotational movements of grip 3 are transferred to catheter probe 1 and in particular to the distal probe region 28, with a resultant bend in the distal end of the probe. As is known from DE 100 45 036 C1, the control element 13 can preferably be torsion-resistant in its longitudinal axis, such that rotations of grip 3 are transmitted with identical rotation angle as far as the distal end of catheter probe 1. Suitably controllable distal probe ends are also described in DE 201 18 886 or DE 199 28 272 A1.

Figure 4:
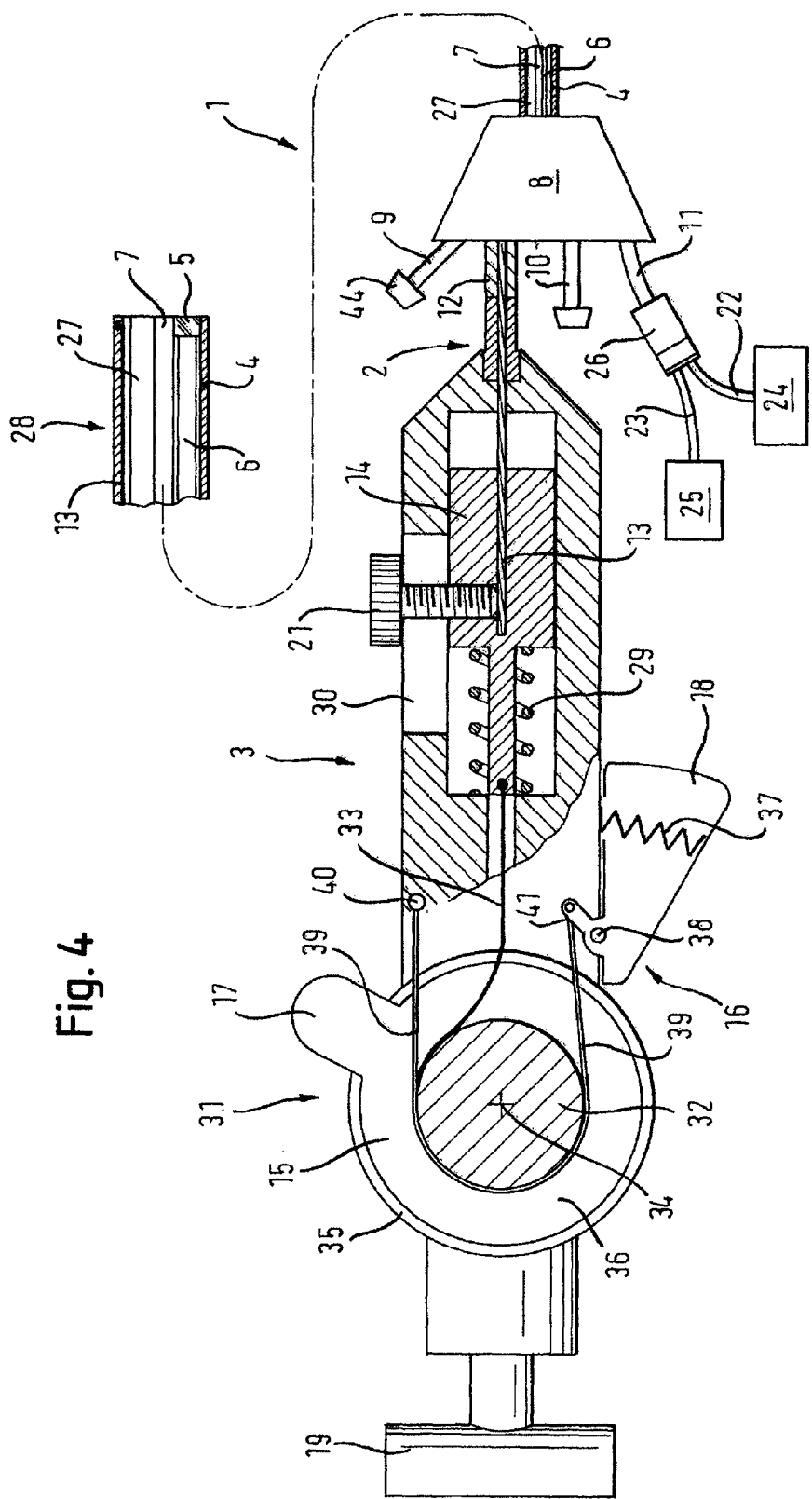
FIG. 4 a partially cutaway view of the grip in FIGS. 1-3, with a catheter probe releasably attached thereto.

As can be seen from FIG. 4 in particular, the proximal end of the control element 13 guided through the tubule-shaped guide device 12 is fixedly attached by means of a releasable fixing means 21, for example in the form of a locking screw, to a slider 14 mounted displaceably in the axial direction. Slider 14 is mounted inside the grip housing and non-rotatingly about the axis of the housing of grip 3. In this way, a non-rotating connection is obtained between grip 3, or the housing of grip 3, and control element 13. Due to the shape, for example of probe attachment member 8, or on the basis of a marking on the catheter probe, for example on probe attachment member 8, it is possible to identify the angular position of the catheter probe, in particular the position of the distal probe end 28 and the angular rotational position of optical system 6 about the probe axis.

Slider 14 is axially movable inside the housing of grip 3 against the biasing force, for example of a biasing spring 29, and is moved and guided in the axial direction. The biasing force acts in the direction of the front (distal) end of grip 3. When the slider is in its frontmost position, the distal probe end 28 is not bent relative to the rest of the probe. When slider 14 is moved against the biasing force of spring 29 in the direction of the rearward (proximal) end of grip 3, this movement is transmitted via control element 13 to the distal probe end 28 and the distal probe end 28 is bent to an extent that depends on the extent of the displacement movement. The slider can be operated by means of an operating element connected to the fixing means, for example with locking screw 21. For example, the head of the locking screw can be dimensioned so that it acts as an operating element. However, an additional operating element can also be provided. The operating element can project through a longitudinal slot 30 extending axially within the grip housing, as shown for the locking screw 21 functioning as a releasable fixing means in FIGS. 1 and 2. At its two ends, said longitudinal slot 30 can form stops for limiting the movement of slider 14 and the axial controlling movement of control element 13. The releasable fixing means 21 shown in the form of a locking screw projecting through the longitudinal slot 30 of the grip housing makes it easier to attach the proximal end of control element 13 to the slider 14.

In the embodiment shown, the axial slider movement is generated by a crank assembly 31 with which a pivoting movement or rotational movement produced at the outer part of the grip is converted into the axial, linearly acting slider movement. The crank assembly 31 used in the embodiment has a winding member 32 onto which a traction means 33 in the form of a cable, a wire or a tape can be wound. One end of traction means 33 is fixedly attached to winding member 32 and the other end of the traction means 32 is fixedly attached to slider 14. An operating element 17 pivotably mounted on the outside of grip 3 is fixedly attached to winding member 32. In the embodiment shown, operating element 17 has an operating bracket extending parallel to the axis 32 of the winding member. Axis 34 and operating element 17 lie transversely (perpendicularly) to the longitudinal extension of the elongated, in particular tubular shaped grip housing. Operating element 17 is fixedly attached at both ends to the roller-shaped winding member 32. For this purpose, winding member 32 can extend at its two ends beyond its hollow cylindrical bearing 35 on the housing. However, it is also possible to attach the U-shaped operating element 17 to winding member 32 via end plates 36 fixedly attached to winding member 32 at its two ends. Depending on the pivot angle range of operating element 17 and hence of winding member 32 about its axis 34, slider 14 is axially moved inside the housing. As already explained, this slider movement is transferred to the distal probe end 28 to bend the probe end 28 relative to the remainder of the probe.

The slider movement and hence the bending of the distal probe end 28 can be locked in various positions with the aid of a locking device 16. In the embodiment shown, locking device 16 acts on crank assembly 31, in particular on the position of winding member 32. However, it is also possible to provide a locking device that acts directly on slider 14, for example in the form of a locking screw, clamping lever or the like.

The locking device 16 shown in the embodiment in FIG. 4 contains a friction tape 39 that is partially coiled around winding member 32, for example with a contact angle of approximately 180°. One tape end 40 is fixated on the grip housing and the other tape end 41 is attached to an operating element 18 designed as a double-armed lever, for example an L-shaped lever. Operating element 18 is pivotably mounted on the grip housing in a lever axis 38. A spring 37 acts on the one lever arm of operating element 18 such that friction tape 39, which is attached to the other lever arm, is tensioned and thus pressed firmly onto winding member 32 over the range of contact. Due to the static friction between winding member 32 and friction tape 39, winding member 32 and hence slider 14 are locked in the desired position against the force of biasing spring 39. Spring 37, which acts between the grip housing and the one lever arm of operating element 18, imparts the required braking or retention force.

By moving operating element 18 against the force of spring 37, the frictional engagement between friction tape 39 and the roller-shaped winding member 32 is reduced or released, with the result that slider 14 can be moved in the direction of its forward end position due to the biasing force of spring 29, or returned to its forward end position. When this happens, the distal probe end 28 is brought into axial alignment with the rest of the probe. It is also possible to wind traction element 33 onto winding member 32 about an additional pivot angle against the force of biasing spring 29, with slider 14 then being moved to the rearward (proximal) end of grip 3. The distal probe end 28 is then bent further by a corresponding amount. On releasing operating element 18, the retention force imparted by spring 37 via brake strap 39 causes slider 14 to be locked in the new desired position. Of course, it is also possible to exert an actuating force on operating element 17 that overcomes the static friction between brake strap 39 and winding member 32 and thus to terminate the positioning of operating element 17 in the desired position.

Figure 2:
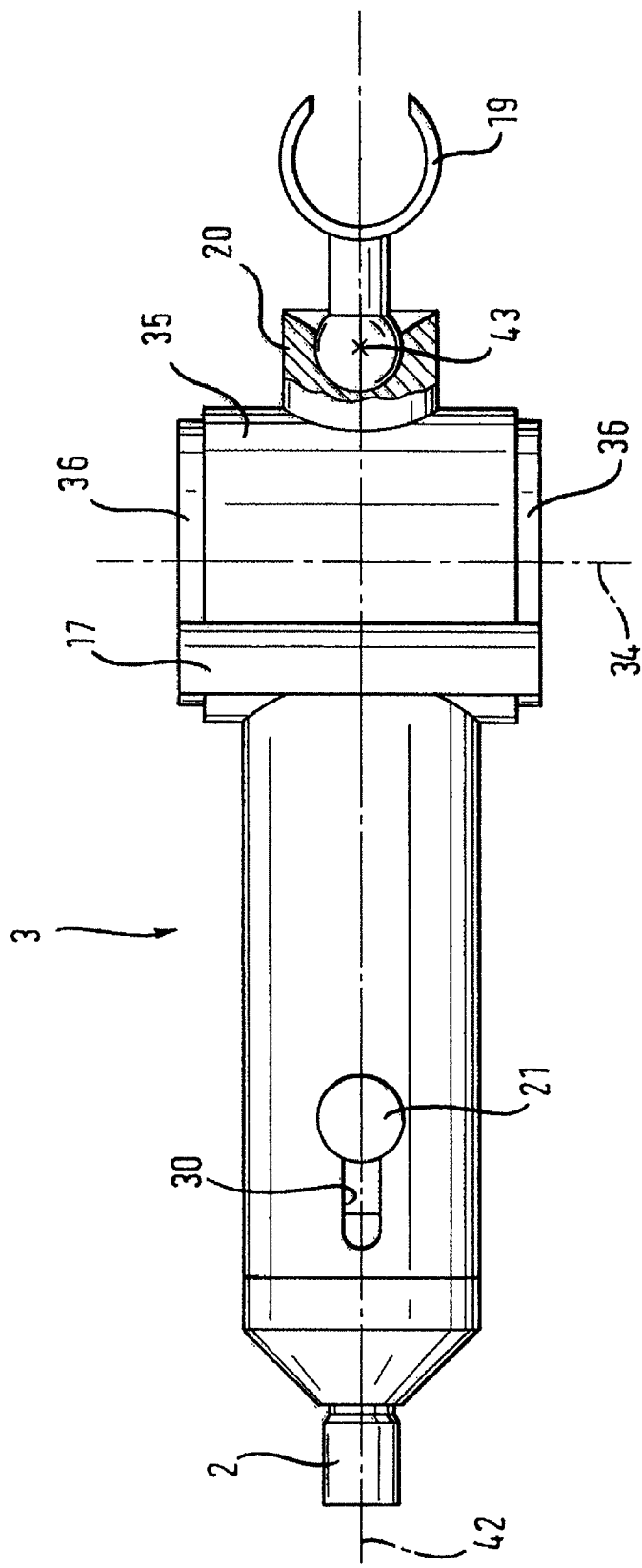
FIG. 2 a plan view from above of the grip shown in FIG. 1.
Figure 3:
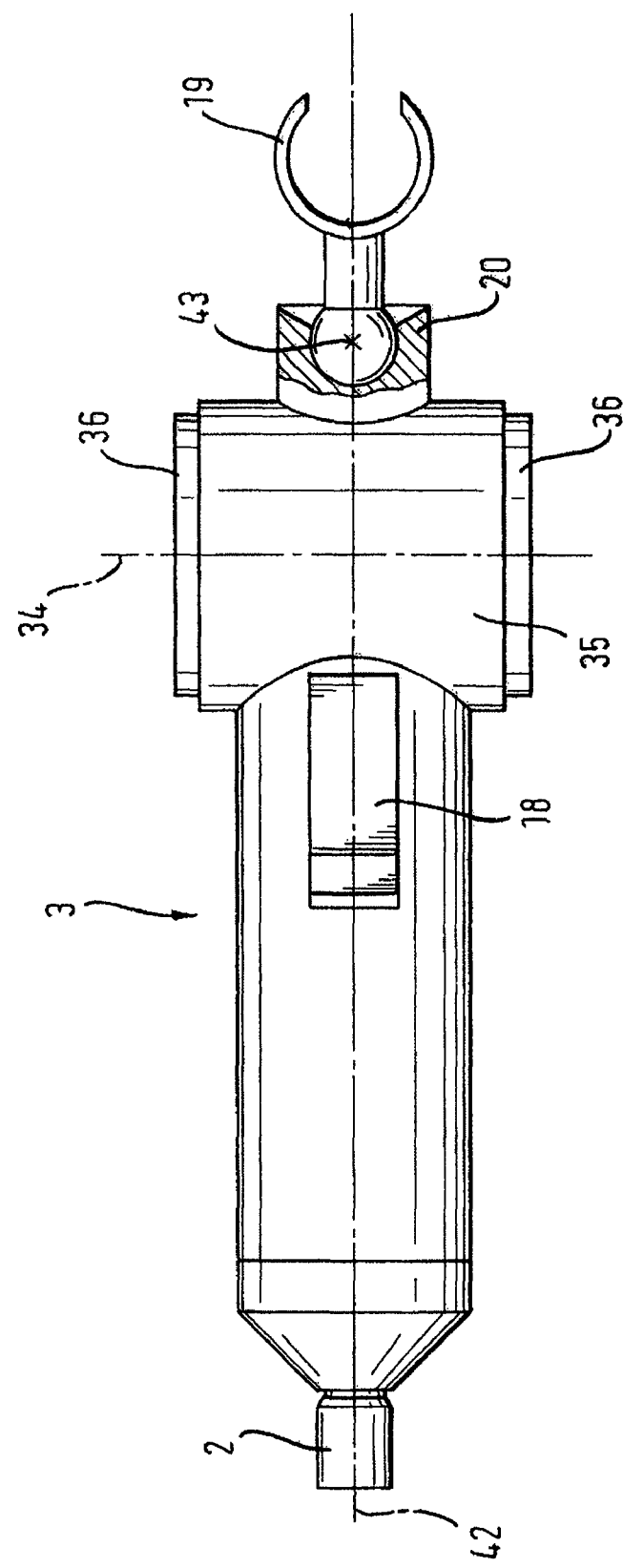
FIG. 3 a view from below of the grip shown in FIGS. 1 and 2.

As can be seen from FIGS. 1-3 in particular, the housing of grip 3, the hollow cylindrical bearing 35 of winding member 32 on the grip housing, and the two operating elements 17 and 18 are designed in such a way that they are symmetric about a center plane 42 through the housing of grip 3. The grip is therefore suitable for both left-handed persons and right-handed persons.

An eyepiece holder 19 can also be pivotably disposed on grip 3, in particular at its rearward (proximal) end. A joint 20, in particular a ball-and-socket joint, is provided for pivotable mounting. A center 43 of the ball-and-socket joint is preferably located in center plane 42, such that identical conditions are provided for both right-handed persons and left-handed persons for pivoting the eyepiece holder 19 into a suitable position.

As FIG. 4 shows, catheter probe 1 is non-rotatingly attached by means of releasable lock 2 to grip 3 only via guide device 12 for control element 13. The other outlets 9, 10 and 11 are independent of grip 3 and can be connected to associated terminal equipment directly using suitable connection means. For example, the proximal lumen outlet 9 for the rinsing/extraction channel can be connected by means of a suitable connection member 44 to a rinsing/extraction device (not shown). A surgical instrument, for example a drill with flexible shaft such as the one known from DE 101 078 156 A1, or an instrument for the removal of foreign matter or comminution of foreign matter, in particular for use in mechanical lithotripsia, can be removably inserted through the proximal lumen outlet 10.

A fiber optic strand for laser irradiation for laser treatment at the destination site can also be introduced into working lumen 7 through lumen outlet 10. After treatment, the respective surgical instrument can be removed from working lumen 7 for maintenance, for example for decontamination treatment.

Optical System 6, which includes illuminating and observation optics, can be inserted through lumen outlet 11 into optical lumen 4 of probe 1. Separate optical lumens 4 can also be provided for the two stands of the illumination optics 22 and the observation optics 23. The respective distal end of optical lumen 4 is hermetically sealed by a transparent cover 5. This prevents contamination of optical system 6 at the destination site. The rest of optical system 6 is protected against contamination by the sheath formed by catheter probe 1. Optical system 6 can be pushed forward inside optics channel 4, for example with the aid of an optical system slider 26 fitted to optical outlet 11, as far as transparent cover 5, which can be in the form of a glass disk. When the distal probe end 28 is bent, optical system 6 can be adjusted accordingly with the aid of the optical system slider 26, and pulled back into the aligned position when the distal probe end 28 is bent back again. Optical system slider 26 can be designed in the manner described in DE 199 56 516 A1, for example. Inside the optical system slider 26, an elastic biasing force can also operate to ensure that optical system 6 is pushed forward automatically when the distal probe end 28 is bent. When the end of the probe is returned to its straight position, optical system 6 is pushed back against said biasing force. This ensures that optical system 6 always abuts with its distal end the cover or seal 5 with a specific compressive force if necessary.

The proximal end of the strand of illumination optics 22 can be connected to an illumination device 24. The proximal end of the strand of observation optics 23 can be connected to an observation device 25. Said observation device 25 can be, for example, an eyepiece that is attachable to eyepiece holder 19. Observation device 25 can also take the form of a camera/monitor system. As FIG. 4 shows, outlets 9, 10 and 11 are not connected to grip 3.

Due to the fact that catheter probe 1 and the proximal probe attachment member 8 with its associated lumen outlets 9, 10 and 11 and guide device 12 as a disposable part can be manufactured using injection molding technology, for example, all that remains for decontamination treatment is the surgical instrument being used. Grip 3 is designed in such a way that it can be used with different catheter probes having a control element like control element 13.

The endoscope described herein can be used, for example, in the endoscope treatment of coronary arteries, in which the catheter probe can be fitted at its distal probe region with a balloon, as known for example from U.S. Pat. No. 4,762,120.

The grip can also be used in conjunction with catheter probes for use in cholangioscopy and mechanical lithotripsia, and particularly in mechanical percutaneous lithotripsia.

To perform such mechanical lithotripsia, catheter probe 1 with observation enabled by optical system 6 and observation device 23 is guided to the location of the foreign body 45 to be removed, in particular a stone, as illustrated by FIG. 5. An outer sleeve 46 is pushed to the vicinity of the proximal end via that portion of the probe which is not inserted into the patient's body. Said outer sleeve 46 has a length that is at least equal to the length of probe inserted into the body. In step (A), the foreign body or stone is gripped with the aid of a gripping tool 47, for example an endoscopic basket that is pushed through working lumen 7 and which projects beyond the distal end of the working lumen. Outer sleeve 46, which preferably is likewise flexible and pliable, is then pushed in step (B) until it contacts stone 45, with a proximal end member of outer tube 46 projected beyond the body opening through which catheter probe 1 has been introduced. Catheter probe 1 is then removed from the patient's body in step (C), with outer sleeve 45 being left in its position contacting basket 47 with the gripped stone 45. A traction wire 48 connected to the basket, or some other connected traction means projects through outer sleeve 46 from the proximal end of outer tube 46. After removal of catheter probe 1, a spiral 49 or other hollow support element having the same effect, either of which being used in known manner in mechanical lithotripsia, is pushed in step (D), by means of traction wire 48 connected to the basket, through the cavity in outer sleeve 46 until it contacts basket 47. With the aid of a known traction device 50 which engages at the proximal end of the traction wire and is supported at the proximal end of the spiral, a pulling force is exerted in step (E) on basket 47 via traction wire 48, said pulling force causing comminution of the gripped foreign body 45, in particular a stone. Spiral 49 and traction wire 48 are moved relative to each other in this step, with the foreign body 45 to be comminuted being pressed against the distal end of spiral 49. In this way, a mechanical percutaneous lithotripsia can be performed in an advantageous manner. Mechanical lithotripsia of the kind described in the foregoing can also be performed in the fields of urethrorenoscopy and cholangioscopy. Known devices, such as those known from DE 102 41 946 A1 or DE 199 55 614 C1, can be used for the apparatus for performing such mechanical lithotripsia.

LIST OF REFERENCE NUMERALS

1 Catheter probe
2 Releasable lock
3 Grip
4 Optical lumen
5 Transparent cover (seal)
6 Optical system
7 Working lumen
8 Proximal probe attachment member
9 Proximal lumen outlet
10 Proximal lumen outlet
11 Proximal lumen outlet
12 Guide device for control element
13 Control element
14 Slider
15 Crank assembly
16 Locking device
17 Operating element for slider movement
18 Operating element for slider lock
19 Eyepiece holder
20 Joint (ball-and-socket joint)
21 Releasable fixing means (e.g. locking screw)
22 Illumination optics
23 Observation optics
24 Illumination optics
25 Observation device
26 Optic slider
27 Rinsing lumen (rinsing channel)
28 Distal end of the probe
29 Biasing force (spring)
30 Longitudinal slot
31 Crank assembly
32 Winding member
33 Traction means
34 Axis
35 Hollow-cylinder bearing
36 End plates
37 Spring
38 Lever axis
39 Friction tape
40 End of tape
41 End of tape
42 Center plane
43 Centre of the ball-and-socket joint
44 Connecting adapter
45 Foreign body (stone)
46 Outer sleeve
47 Basket
48 Traction wire
49 Helix
50 Traction device

The invention claimed is:

1. Endoscope comprising a flexible catheter probe having a plurality of lumens, a hand grip provided at the proximal end of the probe, an optical system provided in at least one optical lumen of the catheter probe, at least one working lumen for a surgical instrument, and a single elongated control element attached at or near the distal end of the probe for bending the end of the probe and displacably guided in axial direction on the probe, wherein a torsion-resistant probe attachment member is provided at the proximal end of the catheter probe, said member having a plurality of lumen outlets for the probe lumens and a torsion-resistant guide device inside which said single elongated control element is guided at the proximal end of the catheter probe is to be connected non-rotatingly to the hand grip by a releasable lock for a torque proof connection between the catheter probe and the hand grip and the single elongated control element is to be connected by means of a releasable fastener to a slider guided inside the hand grip, that the distal end of the optical lumen has a transparent seal, and that the optical system is displaceably disposed inside the optical lumen and can be removed from the optical lumen, wherein the slider is displacably mounted on a housing of the hand grin by a device for converting a rotational movement into a linear axial movement, including a crank assembly.

2. Endoscope according to claim 1, wherein the surgical instrument is removable from at least one working lumen.

3. Endoscope according to claim 1, wherein the catheter probe is configured as a disposable part.

4. Endoscope according to claim 1, wherein the catheter probe is configured as an injection-molded part or extruded part.

5. Endoscope according to claim 1, wherein the slider can be moved against a biasing force of an operating element guided on a housing of the hand grip.

6. Endoscope according to claim 1, wherein the slider can be locked in different positions on a housing of the hand grip by a locking device.

7. Endoscope according to claim 1, wherein a housing of the hand grip and operating elements disposed on the hand grip for actuating the slider movement and for locking the slider movement relative to a center plane running through the hand grip are symmetrically configured.

8. Endoscope according to claim 1, wherein an eyepiece holder is disposed at the proximal end of a housing of the hand grip in a joint, including a ball-and-socket joint.

9. Endoscope according to the claim 8, wherein a center of the ball-and-socket joint is in the center plane running through the hand grip.

10. Endoscope according to the claim 1, wherein a rotational axis of the crank assembly runs perpendicularly to a center plane running through the hand grip.

11. Endoscope according to claim 1, wherein the crank assembly is mounted rotatably about a rotational axis in a hollow cylindrical bearing forming part of the hand grip housing.

12. Endoscope according to claim 1, wherein the lumen outlets for the plurality of probe lumens can be connected to associated terminal equipment independently of the hand grip and external to the hand grip.

13. Endoscope according to claim 1, further comprising a device for mechanical lithotripsia and an outer sleeve tube which can be slid over the catheter probe.

14. Endoscope according to claim 13, wherein the outer sleeve is longer than the length of the catheter probe to be inserted into the patient's body.

15. Endoscope comprising a flexible catheter probe having a plurality of lumens, a hand grip provided at the proximal end of the probe, an optical system provided in at least one optical lumen of the catheter probe, at least one working lumen for a surgical instrument, and a single elongated control element attached at or near the distal end of the probe for bending the end of the probe and displacably guided in axial direction on the probe, wherein a torsion-resistant probe attachment member is provided at the proximal end of the catheter probe, said member having a plurality of lumen outlets for the probe lumens and a torsion-resistant guide device inside which said single elongated control element is guided at the proximal end of the catheter probe is to be connected non-rotatingly to the hand grip by a releasable lock for a torque proof connection between the catheter probe and the hand grip and the single elongated control element is to be connected by means of a releasable fastener to a slider guided inside the hand grip, that the distal end of the optical lumen has a transparent seal, and that the optical system is displaceably disposed inside the optical lumen and can be removed from the optical lumen, wherein the slider can be locked in different positions on a housing of the hand grip by a locking device.

16. Endoscope comprising a flexible catheter probe having a plurality of lumens, a hand grip provided at the proximal end of the probe, an optical system provided in at least one optical lumen of the catheter probe, at least one working lumen for a surgical instrument, and a single elongated control element attached at or near the distal end of the probe for bending the end of the probe and displacably guided in axial direction on the probe, wherein a torsion-resistant probe attachment member is provided at the proximal end of the catheter probe, said member having a plurality of lumen outlets for the probe lumens and a torsion-resistant guide device inside which said single elongated control element is guided at the proximal end of the catheter probe is to be connected non-rotatingly to the hand grip by a releasable lock for a torque proof connection between the catheter probe and the hand grip and the single elongated control element is to be connected by means of a releasable fastener to a slider guided inside the hand grip, that the distal end of the optical lumen has a transparent seal, and that the optical system is displaceably disposed inside the optical lumen and can be removed from the optical lumen, wherein a housing of the hand grip and operating elements disposed on the hand grip for actuating the slider movement and for locking the slider movement relative to a center plane running through the hand grip are symmetrically configured.

* * * * *